(12) United States Patent
Sklar

(10) Patent No.: US 6,939,379 B2
(45) Date of Patent: Sep. 6, 2005

(54) GRAFT LIGAMENT ANCHOR AND METHOD FOR ATTACHING A GRAFT LIGAMENT TO A BONE

(76) Inventor: Joseph H. Sklar, 210 Park Dr., Longmeadow, MA (US) 01106

( * ) Notice: Subject to any disclaimer, the term of this patent is extended or adjusted under 35 U.S.C. 154(b) by 0 days.

(21) Appl. No.: 10/391,173

(22) Filed: Mar. 18, 2003

(65) Prior Publication Data

US 2003/0191530 A1 Oct. 9, 2003

Related U.S. Application Data

(63) Continuation of application No. 09/248,523, filed on Feb. 9, 1999, now Pat. No. 6,533,816.

(51) Int. Cl.[7] .................................................. A61F 2/08
(52) U.S. Cl. ...................................... 623/13.14; 606/72
(58) Field of Search ............................... 606/60, 71, 72, 606/73, 75; 623/13.11–13.2, 13; 411/36, 302

(56) References Cited

U.S. PATENT DOCUMENTS

| RE13,204 E | 2/1911 | Jossart |
|---|---|---|
| 2,353,851 A | 7/1944 | Rosan |
| 3,153,975 A | 10/1964 | Rapata |
| 3,199,398 A | 8/1965 | Weisz |

(Continued)

FOREIGN PATENT DOCUMENTS

| CA | 1015989 | 8/1977 |
|---|---|---|
| DE | 8914308 | 3/1990 |
| EP | 596177 | 5/1994 |
| EP | 0834281 | 8/1998 |
| FR | 2590792 | 6/1987 |
| FR | 2636835 | 3/1990 |
| JP | 5-300917 | 11/1993 |
| WO | WO 98/23229 | 6/1998 |

*Primary Examiner*—David J. Isabella
(74) *Attorney, Agent, or Firm*—Pandiscio & Pandiscio, P.C

(57) ABSTRACT

A graft ligament anchor includes a tubular body having a bore therethrough and proximal and distal ends. A flange is attached to the tubular body at the proximal end thereof and extends radially outwardly beyond the tubular body. A deformable wall is disposed in the tubular body bore and defines, at least in part, a chamber for retaining the graft ligament therein. An expansion device is configured for insertion into the tubular body axially of the tubular body, and for impinging upon the deformable wall to press the deformable wall, and hence the graft ligament received in the chamber, toward a wall of the bore, whereby to fix the graft ligament in the tubular body.

21 Claims, 10 Drawing Sheets

U.S. PATENT DOCUMENTS

| | | | |
|---|---|---|---|
| 3,411,397 A | | 11/1968 | Birmingham |
| 3,516,324 A | | 6/1970 | Berner |
| 3,678,798 A | | 7/1972 | Van Niel |
| 3,731,724 A | * | 5/1973 | Dorflinger .................. 411/302 |
| 3,765,295 A | | 10/1973 | Ptak |
| 3,942,407 A | * | 3/1976 | Mortensen .................. 411/36 |
| 3,976,079 A | | 8/1976 | Samuels et al. |
| 4,083,289 A | | 4/1978 | Erickson |
| 4,085,651 A | | 4/1978 | Koscik |
| 4,407,618 A | | 10/1983 | Kimura |
| 4,535,925 A | | 8/1985 | Ramey et al. |
| 4,580,936 A | | 4/1986 | Francis et al. |
| 4,590,928 A | | 5/1986 | Hunt et al. |
| 4,708,132 A | | 11/1987 | Silvestrini |
| 4,716,893 A | * | 1/1988 | Fischer et al. ................ 606/66 |
| 4,744,793 A | * | 5/1988 | Parr et al. ................ 623/13.14 |
| 4,755,183 A | | 7/1988 | Kenna |
| 4,778,468 A | | 10/1988 | Hunt et al. |
| 4,784,126 A | | 11/1988 | Hourahane |
| 4,828,562 A | | 5/1989 | Kenna |
| 4,851,005 A | | 7/1989 | Hunt et al. |
| 4,870,957 A | | 10/1989 | Goble et al. |
| 4,927,421 A | | 5/1990 | Goble et al. |
| 4,940,467 A | | 7/1990 | Tronzo |
| 4,944,742 A | | 7/1990 | Clemow et al. |
| 4,950,270 A | | 8/1990 | Bowman et al. |
| 4,950,271 A | | 8/1990 | Lewis et al. |
| 5,013,316 A | | 5/1991 | Goble et al. |
| 5,037,422 A | | 8/1991 | Hayhurst et al. |
| 5,062,843 A | | 11/1991 | Mahony, III |
| 5,147,362 A | | 9/1992 | Goble |
| 5,151,104 A | | 9/1992 | Kenna |
| 5,152,790 A | | 10/1992 | Rosenberg et al. |
| 5,211,647 A | | 5/1993 | Schmieding |
| 5,234,430 A | | 8/1993 | Huebner |
| 5,236,445 A | | 8/1993 | Hayhurst et al. |
| 5,268,001 A | | 12/1993 | Nicholson et al. |
| 5,282,802 A | | 2/1994 | Mahony, III |
| 5,312,438 A | | 5/1994 | Johnson |
| 5,324,308 A | | 6/1994 | Pierce |
| 5,356,435 A | | 10/1994 | Thein |
| 5,360,448 A | | 11/1994 | Thramann |
| 5,376,119 A | | 12/1994 | Zimmermann et al. |
| 5,383,878 A | | 1/1995 | Roger et al. |
| 5,425,707 A | | 6/1995 | Goldberg |
| 5,425,767 A | | 6/1995 | Steininger et al. |
| 5,458,601 A | | 10/1995 | Young, Jr. et al. |
| 5,632,748 A | | 5/1997 | Beck, Jr. et al. |
| 5,645,589 A | | 7/1997 | Li |
| 5,702,397 A | | 12/1997 | Goble et al. |
| 5,707,395 A | | 1/1998 | Li |
| 5,776,196 A | | 7/1998 | Matsuzaki et al. |
| 5,899,938 A | | 5/1999 | Sklar et al. |
| 5,906,632 A | | 5/1999 | Bolton |
| 6,355,066 B1 | * | 3/2002 | Kim ....................... 623/13.14 |

* cited by examiner

GRAFT LIGAMENT ANCHOR AND METHOD FOR ATTACHING A GRAFT LIGAMENT TO A BONE

This is a continuation of pending prior U.S. patent application Ser. No. 09/248,523, filed Feb. 09, 1999 now abandoned U.S. Pat. No. 6,533,816 by Joseph H. Sklar for GRAFT LIGAMENT ANCHOR AND METHOD FOR ATTACHING A GRAFT LIGAMENT TO A BONE.

FIELD OF THE INVENTION

This invention relates to medical apparatus and methods in general, and more particularly to apparatus and methods for reconstructing ligaments.

BACKGROUND OF THE INVENTION

Ligaments are tough bands of tissue which serve to connect the articular extremities of bones, or to support and/or retain organs in place within the body. Ligaments are typically composed of coarse bundles of dense white fibrous tissue which are disposed in a parallel or closely interlaced manner, with the fibrous tissue being pliant and flexible but not significantly extensible.

In many cases, ligaments are torn or ruptured as a result of accidents. Various procedures have been developed to repair or replace such damaged ligaments.

For example, in the human knee, the anterior and posterior cruciate ligaments (i.e., the "ACL" and "PCL") extend between the top end of the tibia and the bottom end of the femur. The ACL and PCL cooperate, together with other ligaments and soft tissue, to provide both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such procedures, bone tunnels are generally formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere in the patient; in other circumstances, the graft ligament may be a synthetic device. For the purposes of the present invention, all of the foregoing are collectively referred to as a "graft ligament".

As noted above, the graft ligament may be anchored in place in various ways well known in the art. See, for example, U.S. Pat. No. 4,590,928, issued May 27, 1986 to Michael S. Hunt et al.; U.S. Pat. No. 4,744,793, issued May 17, 1988 to Jack E. Parr et al.; U.S. Pat. No. 4,755,183, issued Jul. 5, 1988 to Robert V. Kenna; U.S. Pat. No. 4,784,126, issued Nov. 15, 1988 to Donald H. Hourahane; U.S. Pat. No. 4,828,562, issued May 9, 1989 to Robert V. Kenna; U.S. Pat. No. 4,927,421, issued May 22, 1990 to E. Marlowe Goble et al.; U.S. Pat. No. 4,950,270, issued Aug. 21, 1990 to Jerald A. Bowman et al.; U.S. Pat. No. 5,062,843, issued Nov. 5, 1991 to Thomas H. Mahony, III; U.S. Pat. No. 5,147,362, issued Sep. 15, 1992 to E. Marlowe Goble; U.S. Pat. No. 5,151,104, issued Sep. 29, 1992 to Robert V. Kenna; U.S. Pat. No. 5,211,647, issued May 18, 1993 to Reinhold Schmieding; and French Patent Publication No. 2,590,792, filed Dec. 4, 1985 by Francis Henri Breard.

Despite the above-identified advances in the art, there remains a need for a graft ligament anchor which is simple in construction, inexpensive to manufacture, and relatively easy to handle and install, while providing safe and effective anchoring of the graft ligament, typically in the knee joint of a mammal.

In addition to the foregoing, it has also been found that the quality of the bone receiving the graft ligament can vary significantly from patient to patient and/or from site to site. In particular, it has been found that in many situations, the bone receiving the graft ligament may be of relatively poor quality, in the sense that the bone is relatively soft and/or lacking in a consistent structure. This can make it difficult to easily and reliably anchor the graft ligament to the bone.

Thus, there also exists a need for a graft ligament anchor which can easily and reliably anchor a graft ligament to a bone of relatively poor quality.

OBJECTS OF THE INVENTION

Accordingly, one object of the present invention is to provide an improved graft ligament anchor which is relatively simple in construction, inexpensive to manufacture, and relatively easy to handle and install, and safe and effective in operation.

Another object of the present invention is to provide an improved graft ligament anchor which can easily and reliably anchor a graft ligament to a bone of relatively poor quality.

And another object of the present invention is to provide an improved method for attaching a graft ligament to a bone.

SUMMARY OF THE INVENTION

These and other objects of the present invention are addressed by the provision and use of a novel graft ligament anchor.

In one form of the invention, the graft ligament anchor comprises a tubular body having a bore therethrough and proximal and distal ends, the tubular body being adapted for placement in a bone tunnel proximate an opening thereof on a bone surface; stop apparatus connected to the tubular body for preventing movement of the tubular body further into the bone tunnel after placement of the tubular body in the opening and the bone tunnel; a deformable wall disposed in the tubular body bore and defining at least in part a chamber for receiving a graft ligament therein; and an expansion device for insertion into the tubular body axially of the tubular body, for impinging upon the deformable wall so as to press the deformable wall, and hence the graft ligament received in the chamber, toward a wall of the bore, whereby to fix the graft ligament in the tubular body.

In accordance with a further feature of the invention, there is provided a method for securing a graft ligament in a bone tunnel having an end opening on a bone surface, a free end of the graft ligament extending out of the bone tunnel end opening. The method comprises providing a graft ligament anchor comprising a tubular body having a bore therethrough and proximal and distal ends; stop apparatus connected to the tubular body for preventing movement of the tubular body further into the bone tunnel after placement of the tubular body in the opening and the bone tunnel; a deformable wall disposed in the tubular body bore and defining at least in part a chamber for receiving the graft ligament therein; and an expansion device for insertion into the tubular body axially of the tubular body, for impinging upon the deformable wall so as to press the deformable wall, and hence the graft ligament received in the chamber, toward a wall of the bore, whereby to fix the graft ligament in the tubular body. The method further comprises the steps of extending the graft ligament free end through the chamber; placing the tubular body in the bone tunnel end opening and in the bone tunnel such that the stop apparatus engages the bone; pulling the graft ligament taut; and inserting the expansion device into the tubular body and advancing the expansion device therein so as to press the deformable wall, and hence the graft ligament received in the chamber, toward the wall of the bore, whereby to fix the graft ligament in the bone tunnel.

In another form of the invention, the graft ligament anchor comprises a tubular body having a bore therethrough and proximal and distal ends. An annular flange is attached to the tubular body at the proximal end thereof and extends radially outwardly beyond the tubular body. A deformable wall is disposed in the tubular body bore and defines, at least in part, a chamber for receiving the graft ligament therein. An expansion device is adapted for insertion into the tubular body, axially of the tubular body, for impinging upon the deformable wall so as to press the deformable wall, and hence the graft ligament received in the chamber, toward a wall of the bore, whereby to fix the graft ligament in the tubular body.

In accordance with a further feature of the invention, there is provided a method for securing a graft ligament in a bone tunnel having an end opening on a bone surface, a free end of the graft ligament extending out of the bone tunnel end opening. The method comprises providing a graft ligament anchor comprising a tubular body having a bore therethrough and proximal and distal ends; an annular flange attached to the tubular body at the proximal end thereof and extending radially outwardly beyond the tubular body; a deformable wall disposed in the tubular body bore and defining at least in part a chamber for receiving the graft ligament therein; and an expansion device for insertion into the tubular body axially of the tubular body, for impinging upon the deformable wall so as to press the deformable wall, and hence the graft ligament received in the chamber, toward a wall of the bore, whereby to fix the graft ligament in the tubular body. The method further comprises the steps of extending the ligament free end through the chamber; placing the tubular body in the bone tunnel end opening and in the bone tunnel such that the annular flange engages the bone surface; pulling the graft ligament taut; and inserting the expansion device into the tubular body and advancing the expansion device therein so as to press the deformable wall, and hence the graft ligament received in the chamber, toward the wall of the bore, whereby to fix the graft ligament in the bone tunnel.

In accordance with a further feature of the invention, there is provided a graft ligament anchor comprising a tubular body having a bore therethrough and proximal and distal ends, the tubular body being adapted for placement in a bone tunnel proximate an opening therefor on a bone surface; stop apparatus connected to the tubular body for preventing movement of the tubular body further into the bone tunnel after placement of the tubular body in the tunnel; a carrier device for insertion into the tubular body axially of the tubular body and having an external groove therein for receiving a graft ligament, and a central channel extending lengthwise therethrough, the carrier being expandable; and an expansion device for insertion into the carrier device channel when the carrier device is in the tubular body, for expanding the carrier device against an internal wall of the tubular body, whereby to fix the graft ligament in the tubular body.

In accordance with a further feature of the invention, there is provided a method for securing a graft ligament in a bone tunnel having an end opening on a bone surface, a free end of the graft ligament extending out of the bone tunnel end opening, the method comprising the step of providing a graft ligament anchor comprising a tubular body having a bore therethrough and proximal and distal ends, the tubular body being adapted for placement in a bone tunnel proximate an opening therefor on a bone surface; stop apparatus connected to the tubular body for preventing movement of the tubular body further into the bone tunnel after placement of the tubular body in the tunnel; a carrier device for insertion into the tubular body axially of the tubular body and having an external groove therein for receiving a graft ligament, and a central channel extending lengthwise therethrough, the carrier being expandable; and an expansion device for insertion into the carrier device channel when the carrier device is in the tubular body, for expanding the carrier device against an internal wall of the tubular body, whereby to fix the graft ligament in the tubular body. The method further includes the steps of extending the graft ligament free end through the tubular body; placing the tubular body in the bone tunnel end opening and in the bone tunnel such that the stop apparatus engages the bone; extending the ligament free end through the carrier device groove; placing the carrier device in the tubular body; pulling the graft ligament taut; and inserting the expansion device into the carrier device and advancing the expansion device therein to press the carrier device, and hence the graft ligament received in the groove, toward an internal wall of the tubular body, whereby to fix the graft ligament in the bone tunnel.

In accordance with a further feature of the invention, there is provided a graft ligament anchor comprising a tubular body having a bore therethrough and proximal and distal ends; a flange attached to the tubular body at the proximal end thereof and extending outwardly beyond the body; a carrier device for insertion into the tubular body axially of the tubular body and having a lengthwise-extending external groove for receiving the graft ligament therein, and a central channel extending lengthwise therethrough, the carrier device having a deformable side wall; and an expansion device for insertion into the carrier device, when the carrier device is in the tubular body, for impinging upon the deformable wall of the carrier device so as to press the deformable wall, and hence the graft ligament received in the carrier device groove, toward a wall of the tubular body bore, whereby to fix the graft ligament in the tubular body.

In accordance with another feature of the invention, there is provided a method for securing a graft ligament in a bone tunnel having an end opening on a bone surface, a free end of the graft ligament extending out of the bone tunnel end opening. The method comprises the step of providing a graft ligament anchor including a tubular body having a bore therethrough and proximal and distal ends; a flange attached to the tubular body at the proximal end thereof and extending outwardly beyond the body; a carrier device for insertion into the tubular body axially of the tubular body and having a lengthwise-extending exterior groove for receiving the graft ligament therein, and a central channel extending lengthwise therethrough, the carrier device having a deformable side wall; and an expansion device for insertion into the carrier device, when the carrier device is in the tubular body, for impinging upon the deformable wall of the carrier device so as to press the deformable wall, and hence the graft ligament received in the carrier device groove, toward a wall of the tubular body bore, whereby to fix the graft ligament in the tubular body. The method further includes the steps of extending the graft ligament free end through the tubular body; placing the tubular body in the bone tunnel end opening and in the bone tunnel such that the flange engages the bone surface; extending the graft ligament free end through the carrier device groove; placing the carrier device in the tubular body; pulling the graft ligament taut; and inserting the expansion device into the carrier device and advancing the expansion device therein so as to press the carrier device deformable wall, and hence the graft ligament received in the carrier device groove, toward an interior wall of the tubular body, whereby to fix the graft ligament in the bone tunnel.

In accordance with a further feature of the invention, there is provided a graft ligament anchor comprising a tubular body having a bore therethrough, external threads along a length thereof, and proximal and distal ends; a carrier device for insertion into the tubular body axially of the tubular body and having a lengthwise-extending external groove for receiving the graft ligament therein, and a central channel extending lengthwise therethrough, the carrier device having a deformable side wall; and an expansion device for insertion into the carrier device, when the carrier device is in the tubular body, for impinging upon the deformable wall of the carrier device so as to press the deformable wall, and hence the graft ligament received in the carrier device groove, toward a wall of the tubular body bore, whereby to fix the graft ligament in the tubular body.

In accordance with a further feature of the invention, there is provided a method for securing a graft ligament in a bone tunnel having an end opening on a bone surface, a free end of the graft ligament extending out of the bone tunnel end opening. The method comprises the step of providing a graft ligament anchor comprising a tubular body having a bore therethrough, external threads along a length thereof, and proximal and distal ends; a carrier device for insertion into the tubular body axially of the tubular body and having a lengthwise-extending external groove for receiving the graft ligament therein, and a central channel extending lengthwise therethrough, the carrier device having a deformable side wall; and an expansion device for insertion into the carrier device, when the carrier device is in the tubular body, for impinging upon the deformable wall of the carrier device so as to press the deformable wall, and hence the graft ligament received in the carrier device groove, toward a wall of the tubular body bore, whereby to fix the graft ligament in the tubular body. The method further comprises the steps of extending the graft ligament free end through the tubular body; screwing the tubular body into the bone tunnel end opening and into the bone tunnel; extending the ligament free end through the carrier device groove; placing the carrier device in the tubular body; pulling the graft ligament taut; and inserting the expansion device into the carrier device and advancing the expansion device therein so as to press the carrier device deformable wall, and hence the graft ligament received in the groove, toward an interior wall of the tubular body, whereby to fix the graft ligament in the bone tunnel.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
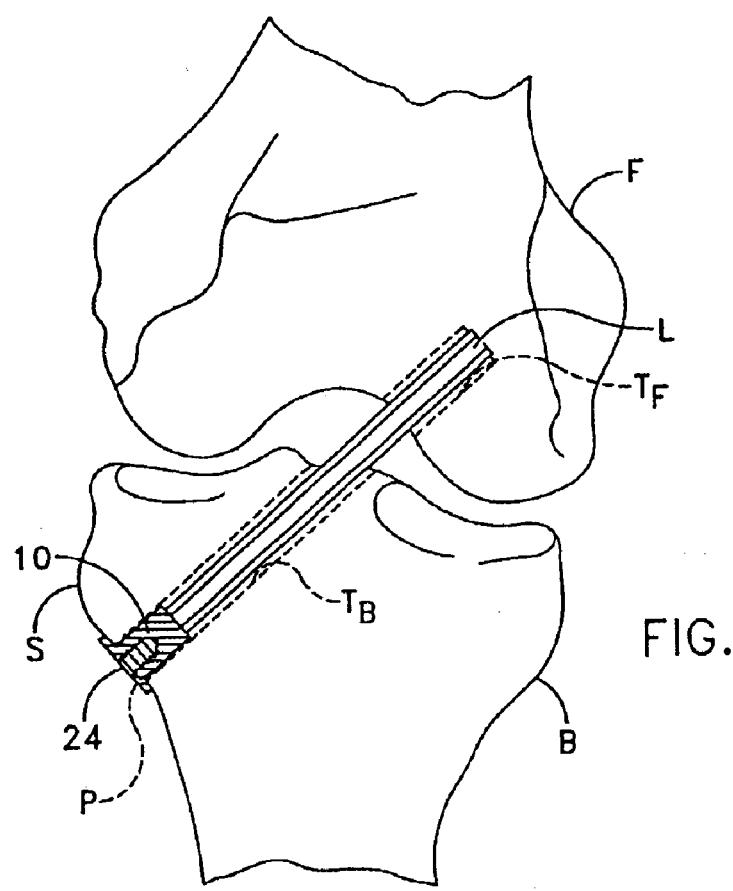
FIG. 1 is a diagrammatic illustration of a ligament anchoring application conducted in accordance with one aspect of the present invention.

Referring first to FIG. 1, it will be seen that in one application of the graft ligament anchor, bone tunnels $T_F$ and $T_B$ are formed in a femur F and tibia B, respectively. A graft ligament L is anchored at one end (not shown) in the femur F by means well known in the art, and extends from femoral tunnel $T_F$ and into tibial tunnel $T_B$ and therethrough. The free end of graft ligament L extending from a tunnel opening P on a tibial surface S must be anchored to tibia B, so that graft ligament L is secured at both ends and essentially duplicates the function of the aforementioned ACL.

Figure 2:
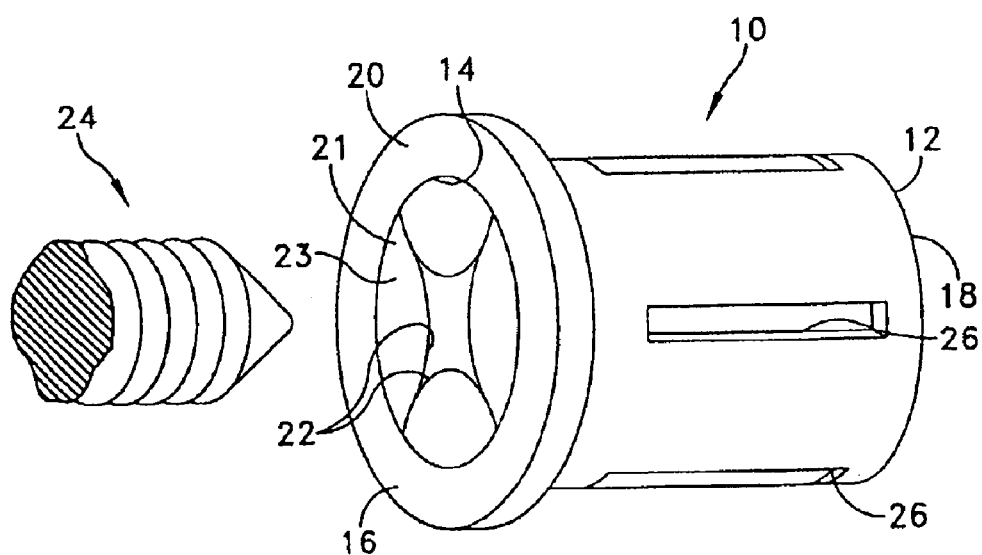
FIG. 2 is an exploded perspective view of one form of graft ligament anchor illustrative of an embodiment of the invention.
Figure 3:
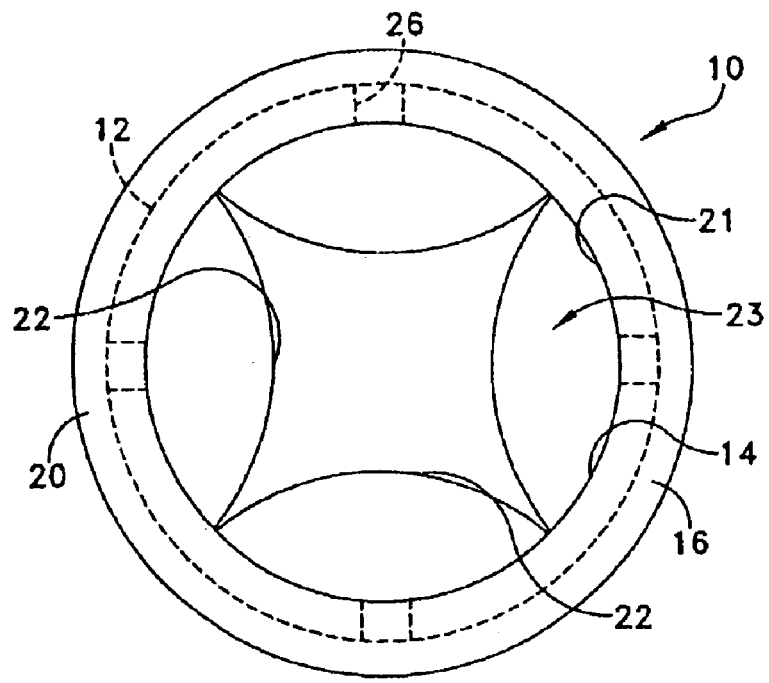
FIG. 3 is an end view of the anchor tubular body portion of FIG. 2.

Referring next to FIGS. 1–3, it will be seen that, in one illustrative embodiment, the inventive graft ligament anchor 10 includes a tubular body 12 having a bore 14 extending therethrough and having a proximal end 16 and a distal end 18. An annular flange 20 is fixed to tubular body 12 at proximal end 16 thereof, and extends radially outwardly beyond body 12. Flange 20 may be continuous, interrupted, or a partial flange, the former being shown in FIGS. 2–8 and the latter being shown in FIG. 9.

One or more deformable walls 22 (four such walls 22 are shown in FIGS. 2 and 3) are formed in tubular body bore 14 and define, in conjunction with tubular interior body wall 21, elongated chambers 23 which extend lengthwise within tubular body 12. Elongated chambers 23 are each adapted to receive and retain a graft ligament L therein.

An expansion device 24 (FIG. 2), such as a wedge, wedge-shaped screw or the like, is adapted for insertion into tubular body 12 axially of the tubular body, for impinging upon deformable walls 22 so as to press deformable walls 22, and hence the graft ligament L received in an elongated chamber 23, toward wall 21 of bore 14, whereby to fix graft ligament L against wall 21, and thereby to fix graft ligament L in tubular body 12.

Tubular body 12 and annular flange 20 may be formed as a single integral unit, preferably of a substantially rigid plastic or metal material.

Figure 8:
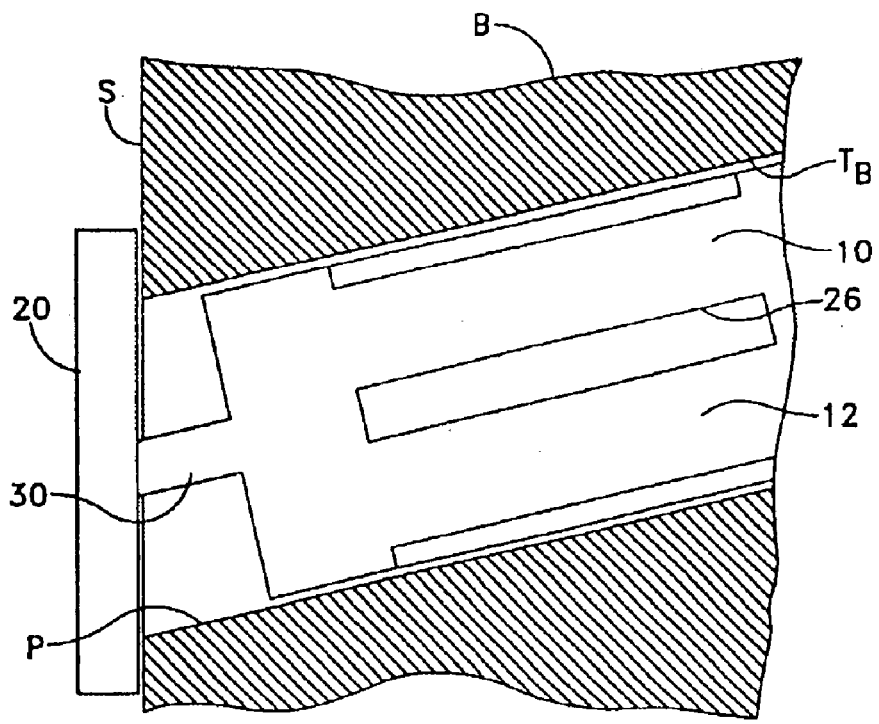
FIG. 8 is a side elevational view of the embodiment of FIG. 7, shown in place in a bone tunnel.
Figure 9:
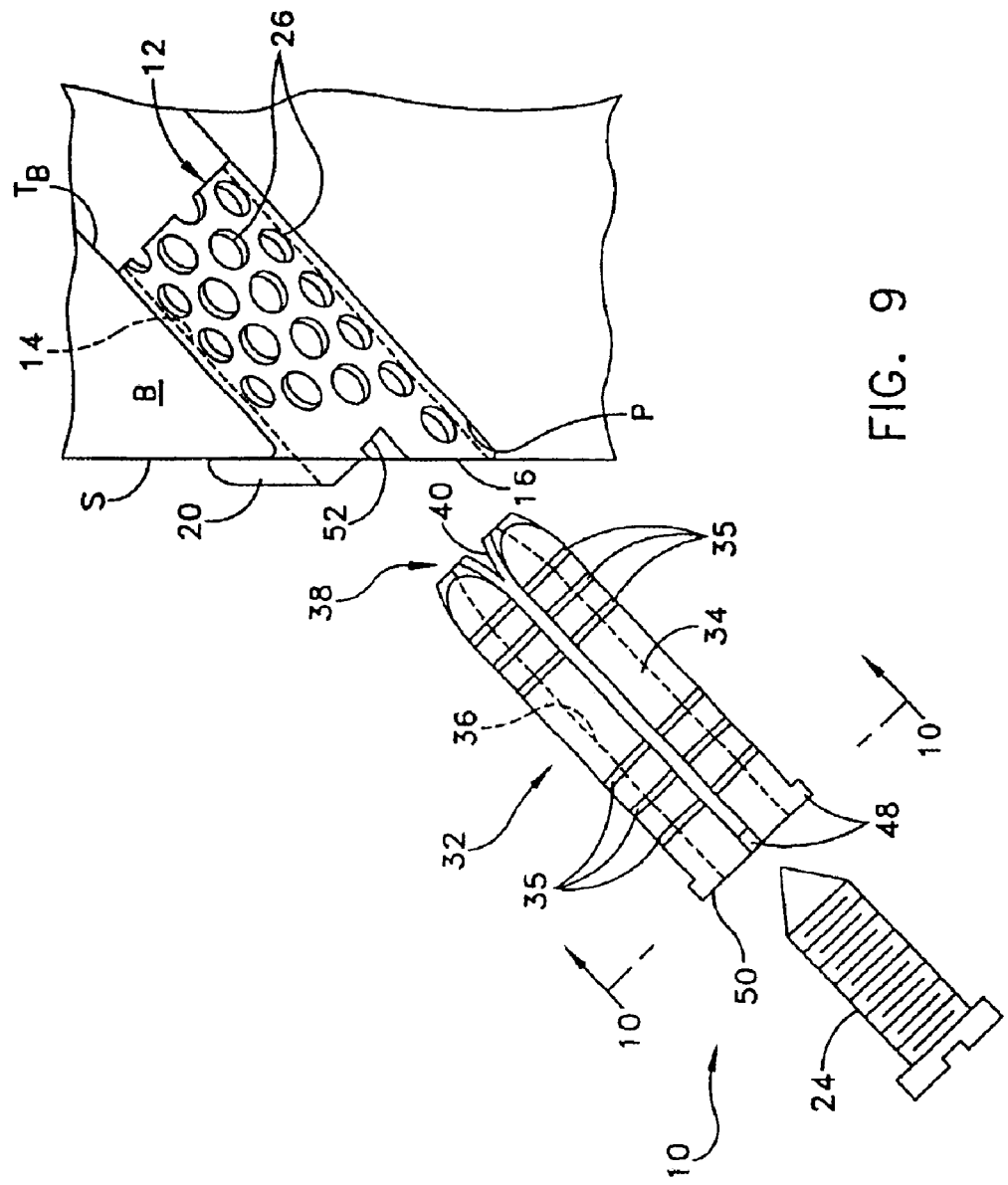
FIG. 9 is an exploded perspective view of another alternative embodiment of graft ligament anchor.

Tubular body 12 may be provided with one or more openings 26 which may be in the form of elongated slots (FIGS. 2, 5, 6, 7 and 8) or orifices (FIG. 9). Openings 26 communicate with the interiors of chambers 23 and permit cells from the bone tunnel walls to migrate into tubular body 12 and chambers 23 during the healing process and further lock graft ligament anchor 10 and graft ligament L in place in tibial tunnel TB. Furthermore, the openings 26 also serve to receive outwardly-pressed portions of the graft ligament L, which helps to further secure the graft ligament L to tubular body 12.

Figure 4:
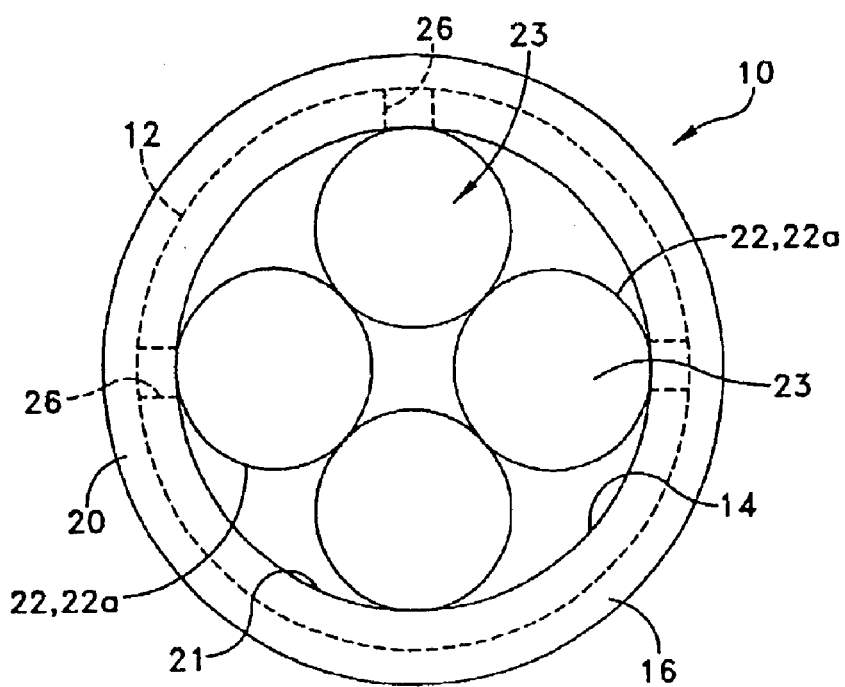
FIG. 4 is an end view of an alternative embodiment of the anchor tubular body portion.

In FIG. 4, there is shown an alternative embodiment of graft ligament anchor 10 in which the deformable walls 22 comprise sleeves 22a defining elongated chambers 23 for receiving and retaining graft ligament L.

Figure 5:
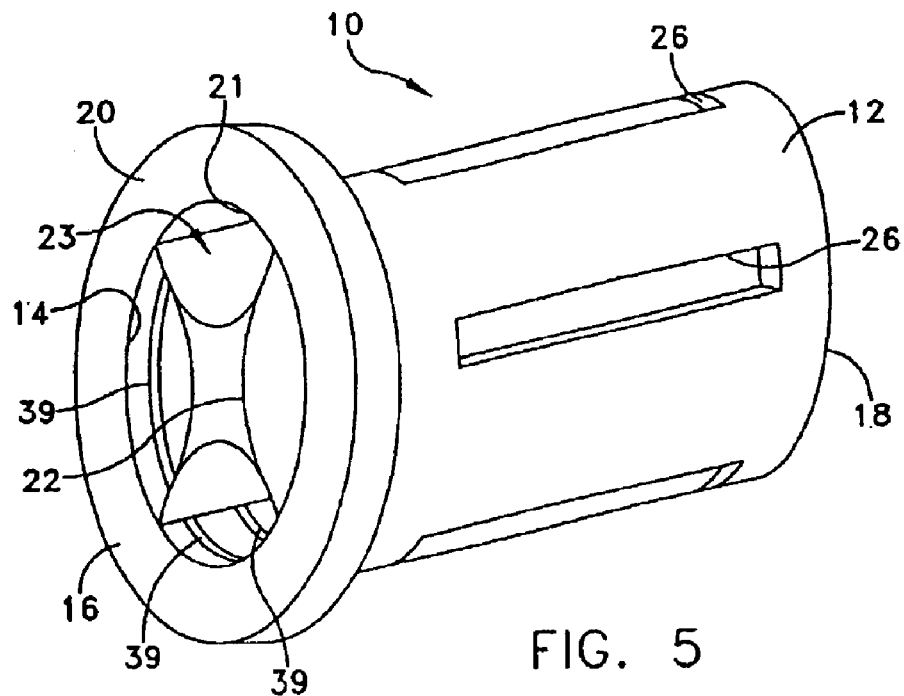
FIG. 5 is a perspective view showing another alternative embodiment of the anchor tubular body portion.
Figure 6:
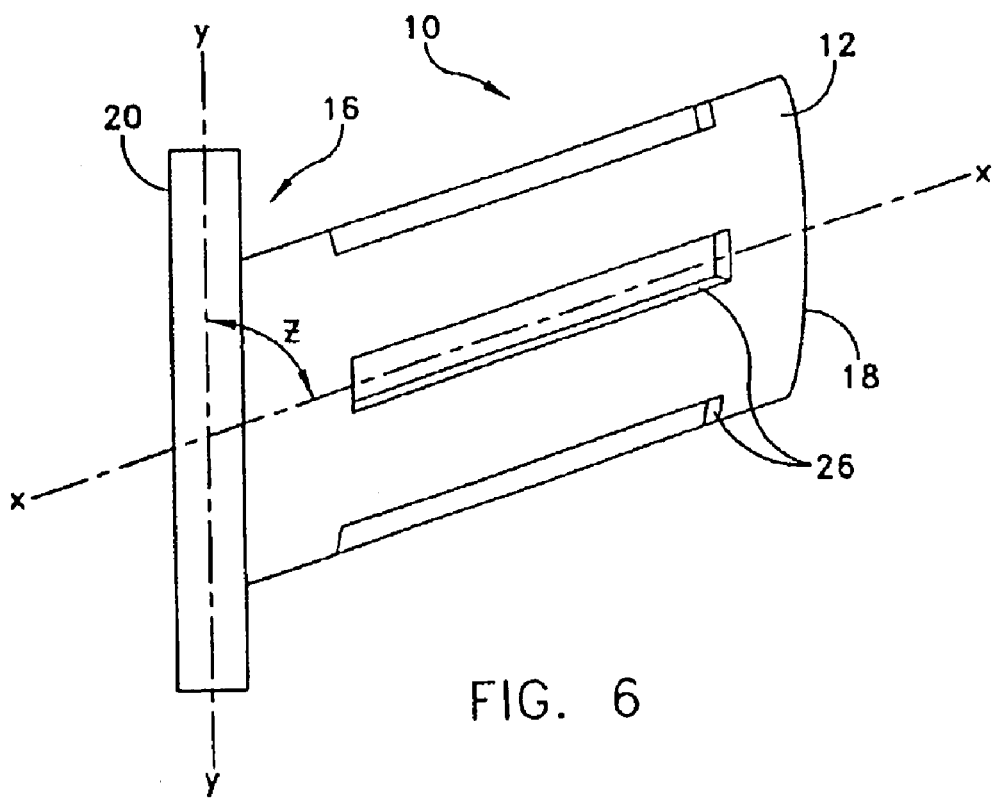
FIG. 6 is a side elevational view of the tubular body portion embodiment of FIG. 5.

Referring next to FIGS. 5 and 6, it will be seen that, in an alternative embodiment of graft ligament anchor 10, the axis x—x of tubular body 12 intersects a plane y—y of annular flange 20 at an acute angle z. The angle z permits flange 20 to lie flat against the tibial surface S, which surface S is typically not normal to the longitudinal axis of tunnel TB in ACL reconstructions. Tubular body 12 may be provided with the aforementioned openings or slots 26, as shown in FIGS. 5 and 6.

Figure 7:
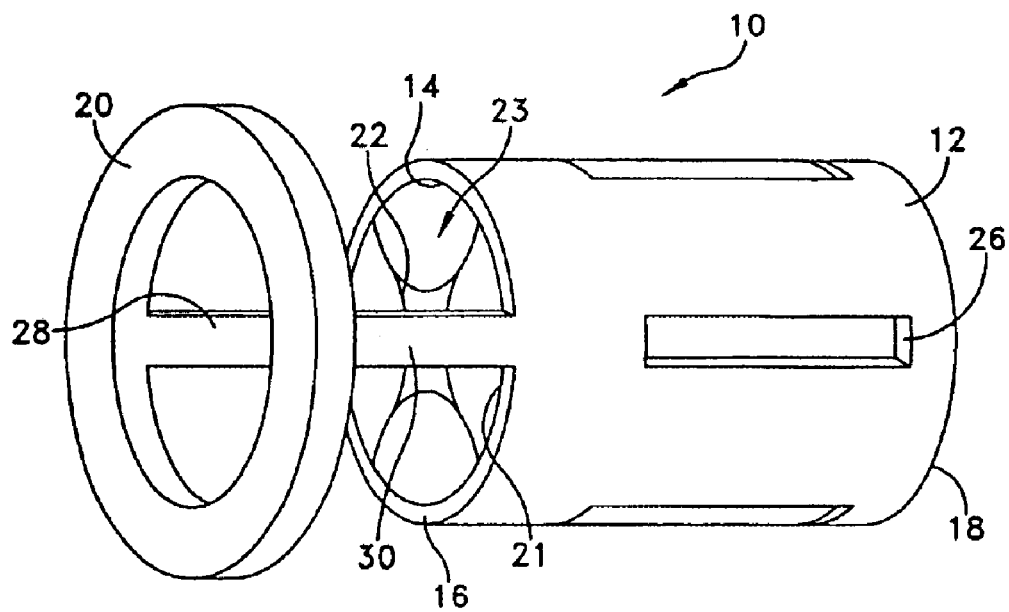
FIG. 7 is a perspective view of another alternative embodiment of the anchor tubular body portion.

Referring next to FIGS. 7 and 8, it will be seen that in another alternative embodiment of graft ligament anchor 10, arms 28, 30 extend axially and proximally from tubular body proximal end 16. Annular flange 20 is mounted on the proximal ends of arms 28, 30. The arms 28, 30, being of relatively thin structure, provide a degree of flexibility, even if made in unitary fashion as extensions of tubular body 12, and permit annular flange 20 to assume a position essentially flat against tibial surface S, while tubular body 12 extends into bone tunnel $T_B$ at an acute angle to the plane of flange 20. Again, as seen in FIG. 8, tubular body 12 of this embodiment of graft ligament anchor 10 may be provided with openings 26 for migration of bone material therethrough.

Figure 8A:
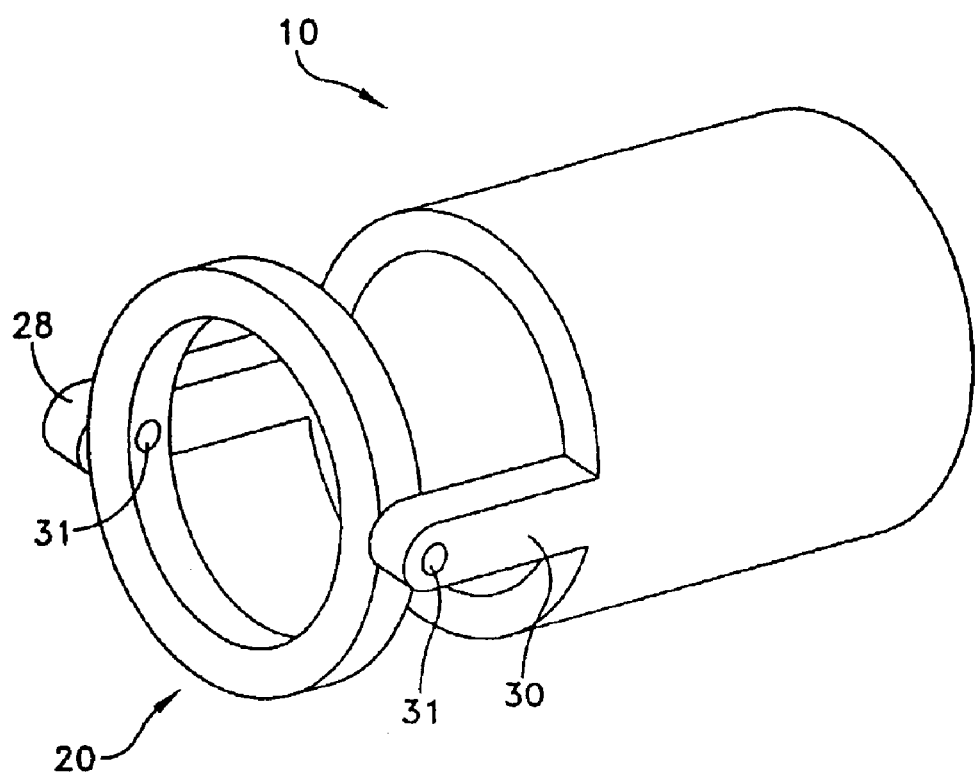
FIG. 8A is a perspective view of another alternative embodiment of the anchor tubular body portion.

Referring next to FIG. 8A, it will be seen that in another alternative embodiment of graft ligament anchor 10, the annular flange 20 is pivotally connected to arms 28, 30 by means of a pair of pins 31. This construction permits arms 28, 30 to be formed relatively thick and rigid, yet permits annular flange 20 to assume a position essentially flat against tibial surface S while tubular body 12 extends into bone tunnel $T_B$ at an acute angle to the plane of flange 20.

In essence, with the embodiment of FIGS. 7 and 8, deflection of arms 28,30 permits flange 20 to assume the desired position relative to tubular body 12, whereas with the embodiment of FIG. 8A, pivot pins 31 permit flange 20 to assume the desired position relative to tubular body 12.

In operation, the graft ligament L is first anchored in the femur F in ways well known in the art, and extended out through tunnels $T_F$ and $T_B$, and out the tunnel opening P. Then the graft ligament L is fed through one of the elongated chambers 23 of tubular body 12. Tubular body 12 is then inserted into tunnel $T_B$ by way of opening P, and advanced in tunnel $T_B$ until flange 20 engages bone surface S. The engagement of flange 20 with bone surface S will prevent tubular body 12 from advancing further into tibia B. The graft ligament L, which extends out of proximal end 16 of tubular body 12, is then pulled taut, and expansion device 24 is advanced into bore 14, engaging deformable walls 22 (or, alternatively, deformable walls 22a) and pressing the deformable walls, and hence the graft ligament L received within one of the elongated chambers 23, toward the interior wall of bore 14. Inasmuch as tubular body 12 is relatively rigid, deformable walls 22 compress against the bore wall and hold the graft ligament in that position.

At this point, graft ligament L will be securely fastened to bone B, inasmuch as (1) expansion device 24 holds graft ligament L securely to tubular body 12, (2) annular flange 20 prevents tubular body 12 from being pulled further into tibia bone B, and (3) the graft ligament L prevents tubular body 12 from falling out of bone tunnel $T_B$. In this respect it should be appreciated that, inasmuch as graft ligament L is typically slightly elastic in nature, and inasmuch as graft ligament L is pulled taut prior to fastening to tubular body 12, graft ligament L will tend to hold tubular body 12 in bone tunnel $T_B$ under tension.

The free end of graft ligament L can then be trimmed off at tibial surface S.

It should be appreciated that once expansion device 24 has been fully inserted into tubular body 12, and once the free end of graft ligament L has been trimmed off at tibial surface S, only annular flange 20 will protrude above tibial surface S. Since annular flange 20 is relatively thin, graft ligament anchor 10 has a low profile relative to tibial surface S. This can be important for patient comfort, particularly inasmuch as relatively little tissue overrides this portion of the patient's tibia.

If the graft ligament anchor is provided with openings 26, cells from the bone tunnel wall can, during the healing process, migrate through openings 26 and into chambers 23 so as to further lock the tubular body and graft ligament in place.

It should be appreciated that the deformable walls 22 (or, alternatively, the deformable walls 22a) of chambers 23 serve to protect the graft ligament L from cutting or other damage by expansion device 24, spread the pressure from expansion device 24 substantially evenly on the graft ligament L, and provide improved friction against the graft ligament.

It should also be appreciated that, inasmuch as expansion device 24 fastens graft ligament L to tubular body 12, and inasmuch as the structural integrity of tubular body 12 can be carefully controlled during the manufacturing process, graft ligament anchor 10 will form a secure attachment even when tibia B has relatively poor bone quality.

It should also be appreciated that, inasmuch as a plurality of elongated chambers 23 are provided in tubular body 12, graft ligament anchor 10 can be used to simultaneously fasten a plurality of graft ligament free ends to tibia B.

Figure 10:
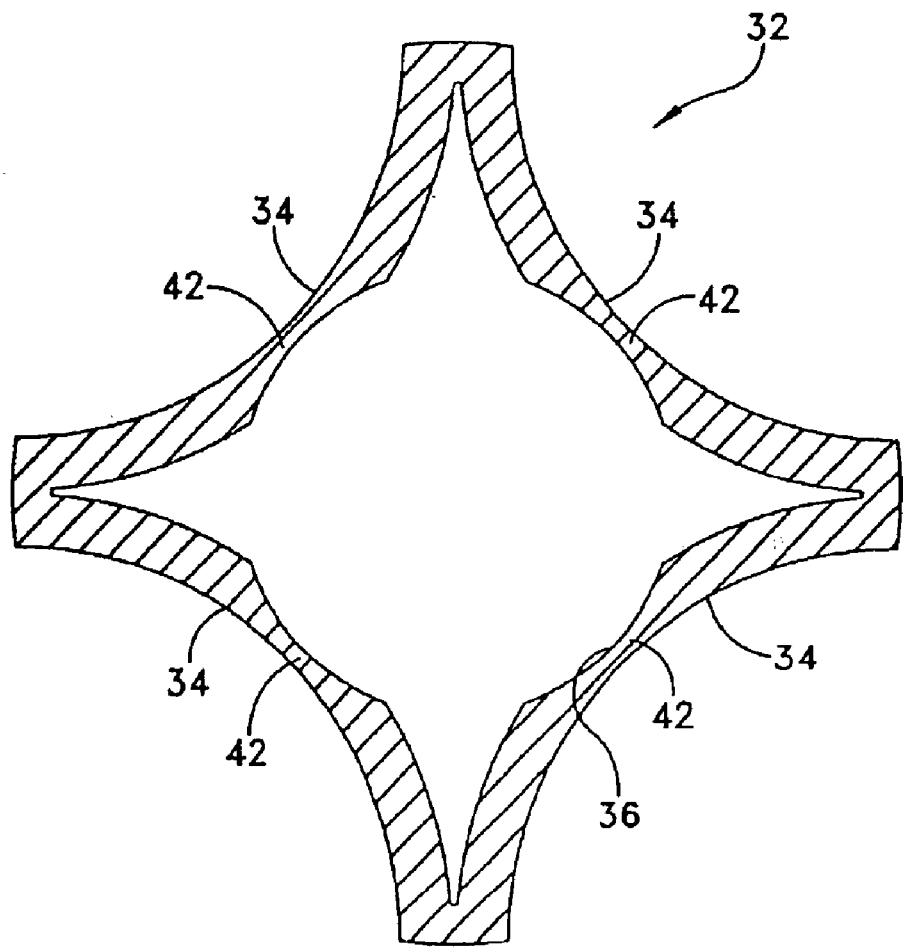
FIG. 10 is a sectional view taken along line 10—10 of FIG. 9.

In FIG. 9, there is shown an alternative embodiment of graft ligament anchor in which flange 20 is a partial flange, deformable walls 22 are omitted from the interior of tubular body 12, and openings 26 in tubular body 12 are in the form of a multitude of orifices. This embodiment includes a ligament carrier 32 having lengthwise-extending grooves 34 formed therein for receiving the graft ligament L which is to be anchored. The grooves 34 each may be provided with widthwise-extending ridges 35 which assist in holding the graft ligament L in a groove 34. Expansion device 24, in this embodiment, is preferably a screw which is driven into a central channel 36 (FIGS. 9 and 10) of ligament carrier 32. The distal end 38 of ligament carrier 32 is provided with slits 40 which permit expansion of ligament carrier 32. Furthermore, as shown in FIG. 10, central channel 36 and outer grooves 34 define thin walls 42 which can expand against a graft ligament L received in an outer groove 34, thereby pressing the graft ligament against the interior wall of tubular body bore 14.

If desired, the tubular bodies 12 may also be provided with interior ridges, such as the interior ridges 39 shown in FIG. 5 or corresponding ridges (not shown) for the embodiment of FIG. 9, disposed on the interior wall of tubular body bore 14, for enhanced engagement with the graft ligament L pressed thereagainst.

Preferably, ligament carrier 32 is provided with a detent 48 extending outwardly from the ligament carrier and disposed near a proximal end 50 of the ligament carrier. Where tubular body 12 is to be used in conjunction with the ligament carrier 32, tubular body 12, at its proximal end 16, is provided with a recess 52 which is complementary to detent 48 and adapted to receive the detent, so as to limit advancement of ligament carrier 32 into tubular body 12.

Preferably, but not necessarily, the length of ligament carrier 32 exceeds the length of tubular body 12, such that when ligament carrier 32 is fully engaged with tubular body 12, a distal portion of ligament carrier 32 extends beyond the distal end of tubular body 12.

In operation, graft ligament L is first anchored in femur F and extended out through tunnels TF and TB and out tunnel opening P. Then graft ligament L is fed through tubular body 12. Next, tubular body 12 is inserted into tunnel TB until flange 20 engages bone surface S (FIG. 9). Then graft ligament L is positioned in one of the outer grooves 34 of ligament carrier 32. Ligament carrier 32 is then inserted into bore 14 of tubular body 12 until the distal end portion of ligament carrier 32 protrudes distally from the distal end of tubular body 12 and carrier detent 48 engages tubular member recess 52, which prevents further advancement of ligament carrier 32 into tubular body 12. Graft ligament L, which extends out of ligament carrier 32 and tubular body 12, is then pulled taut, and expansion device 24 is advanced into the ligament carrier's channel 36, engaging deformable walls 42 and pressing the walls 42, and hence the graft ligament L received in one of the ligament carrier's outer grooves 34, toward the interior wall of bore 14. Inasmuch as tubular body 12 is relatively rigid, deformable walls 42 compress against the interior bore wall of tubular body 12 and hold the graft ligament in that position. At the same time, flange 20 prevents tubular body 12 from being pulled further into tibia B, and the graft ligament prevents tubular body 12 from falling out of bone tunnel $T_B$. In this respect it should be appreciated that, inasmuch as graft ligament L is slightly elastic in nature, and inasmuch as graft ligament L is pulled taut prior to fastening to tubular body 12, graft ligament L will tend to hold tubular body 12 in bone tunnel $T_B$ under tension.

The free end of graft ligament L can then be trimmed off at tibial surface S.

It should be appreciate that, with the foregoing construction, distally of the distal end of tubular body 12, ligament carrier 32 presses the graft ligament directly against interior walls of tibial tunnel TB. Thus, graft ligament L is effectively locked to tubular body 12 and is also pressed directly against the walls of tibial tunnel $T_B$ distal to tubular body 12. This arrangement provides a stress transition for graft ligament L inasmuch as the graft ligament is held in tubular body 12 under relatively high stress, is held under less stress by ligament carrier 32 in tibial tunnel $T_B$ immediately distally of tubular body 12 and, distally of ligament carrier 32, is not pressed against tibial tunnel $T_B$. This transitional arrangement provides improved graft stabilization and immobilization, and helps minimize abrasive movement of the graft ligament against bone surfaces during knee flexure. Furthermore, by providing an enhanced region of direct contact between graft ligament L and the walls of the bone tunnel, biological fixation of the graft ligament to the bone will be enhanced.

It should also be appreciated that once expansion device 24 has been fully inserted into ligament carrier 32, and once the free end of graft ligament L has been trimmed off at tibial surface S, only annular flange 20 will protrude above tibial surface S. Again, since annular flange 20 is relatively thin, graft ligament anchor 10 has a low profile relative to tibial surface S. This can be important for patient comfort, particularly inasmuch as relatively little tissue overrides this portion of the patient's tibia.

It should also be appreciated that, inasmuch as expansion device 24 fastens graft ligament L to tubular body 12, and inasmuch as the structural integrity of tubular body 12 can be carefully controlled during the manufacturing process, the graft ligament anchor shown in FIGS. 9 and 10 will form a secure attachment even when tibia B has relatively poor bone quality.

It should also be appreciated that, inasmuch as a plurality of lengthwise-extending grooves 34 are provided in ligament carrier 32, the graft ligament anchor can be used to simultaneously fasten a plurality of graft ligament free ends to tibia B.

Cells from the bone tunnel wall, in due course, can thereafter migrate through openings 26, and around the graft ligament, so as to further lock tubular body 12 and graft ligament L in place.

Figure 11:
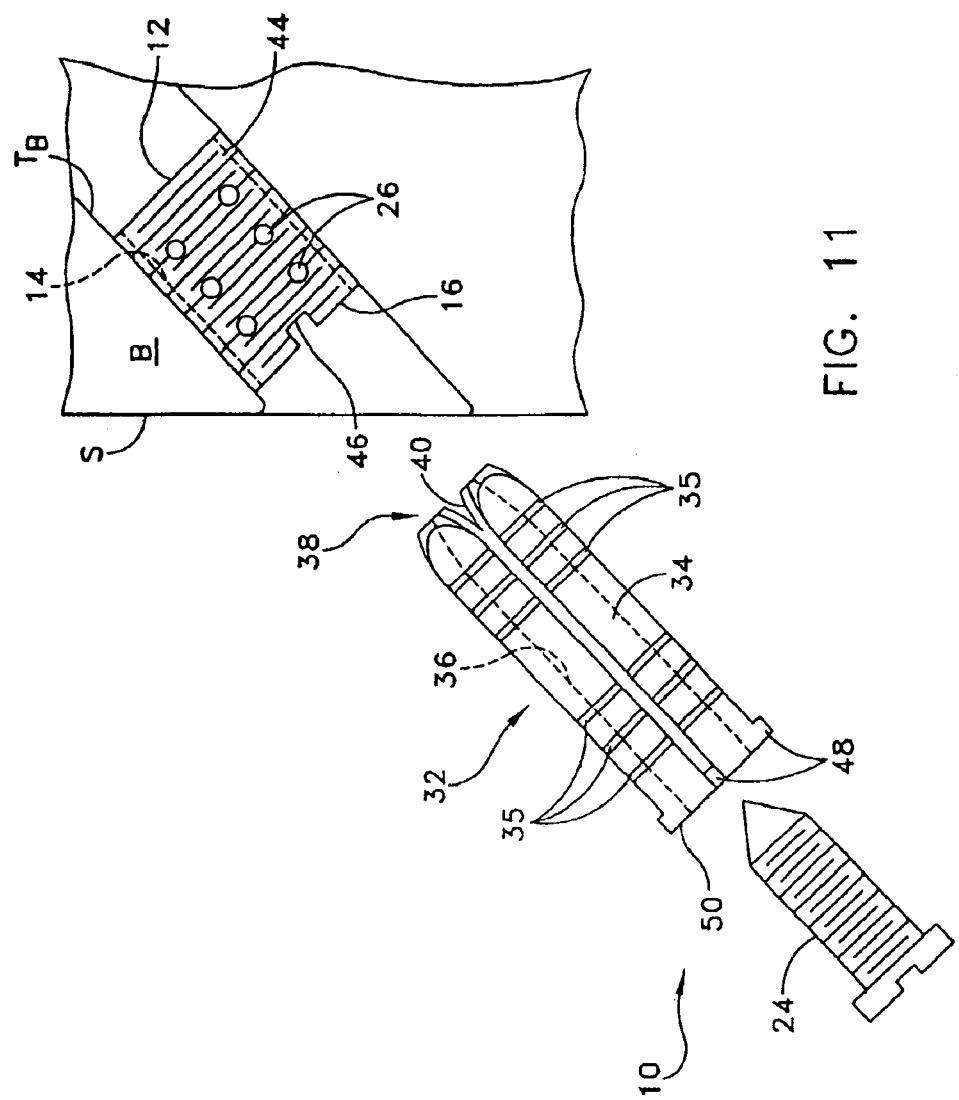
FIG. 11 is similar to FIG. 9, but showing still another alternative embodiment of ligament anchor.

In FIG. 11, there is shown another alternative embodiment of graft ligament anchor, generally similar to the embodiment shown in FIG. 9, but having tubular body portion 12 provided with external screw threads 44 rather than flange 20. The embodiment of FIG. 11 is used in much the same manner as the embodiment of FIG. 9, except that before graft ligament L is anchored in femur F, tubular body 12 is screwed into bone tunnel $T_B$. To facilitate the screwing rotation, tubular body 12 may be provided with slots 46 for receiving a screw driver (not shown). Ligament carrier 32 is provided with one or more detents 48 which is/are complementary to slots 46, and received by slots 46, so as to limit advancement of ligament carrier 32 into tubular body 12. The tubular body 12 may be provided with interior ridges, of the type illustrated in FIG. 5, to assist in the fixation of the graft ligament L to tubular body 12. And tubular body 12 may be provided with openings 26 to permit cells from the bone tunnel walls to migrate into tubular body 12 and to receive outwardly-pressed portions of the graft ligament L, in the manner previously discussed.

In operation, the tubular body 12 is screwed into bone tunnel $T_B$ until proximal end 16 is inboard of bone surface S. Inasmuch as the position of threaded tubular body 12 is easily controlled and unlikely to migrate in the bone tunnel, there is no need for a flange, such as flange 20. Once tubular body 12 is in place, the graft ligament is anchored in the femoral tunnel $T_F$ and the remainder of the operation proceeds substantially as set forth above relative to the embodiment of FIG. 9.

Figure 12:
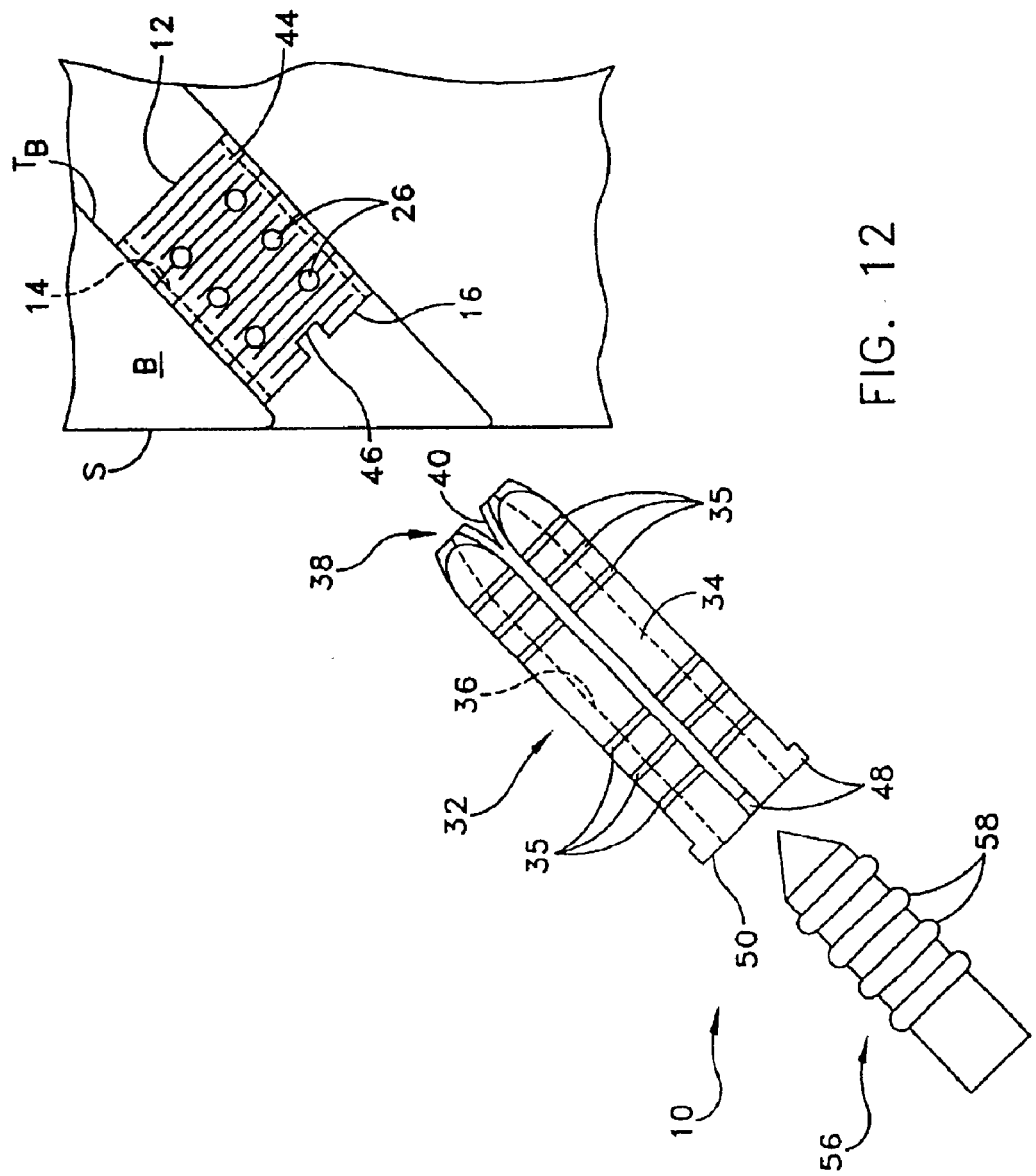
FIG. 12 is similar to FIG. 11, but showing still another alternative embodiment of ligament anchor.

In FIG. 12, there is shown still another alternative embodiment of graft ligament anchor, similar to the embodiments of FIGS. 9 and 11, but wherein the expansion device 24 comprises a mandrel 56, rather than a screw device. The mandrel 56 may be deployed by a gun (not shown) into the carrier 32 and may be provided with ridges 58 for engaging the walls of channel 36 of carrier 32, which walls may include opposing ridges to prevent withdrawal of mandrel 56 from channel 36. Otherwise, the assembly of FIG. 12 is used in much the same manner as the assemblies of FIGS. 9 and 11.

With the embodiments in FIGS. 11 and 12, external screw threads 44 prevent tubular body 12 from being pulled further into bone tunnel $T_B$ under the tension of graft ligament L. To that extent, external screw threads 44 serve the same purpose that external flange 20 serves with the embodiments of FIGS. 1–8, 8A and 9. In this respect it will be appreciated that with the embodiments of FIGS. 11 and 12, once expansion device 24 has been fully inserted into ligament carrier 32, and once the free end of graft liagment L has been trimmed off at tibial surface S, substantially none of the graft ligament anchor will protrude above tibial surface S. This can be important for patient comfort, inasmuch as relatively little tissue overrides this portion of the patient's tibia.

Figure 13:
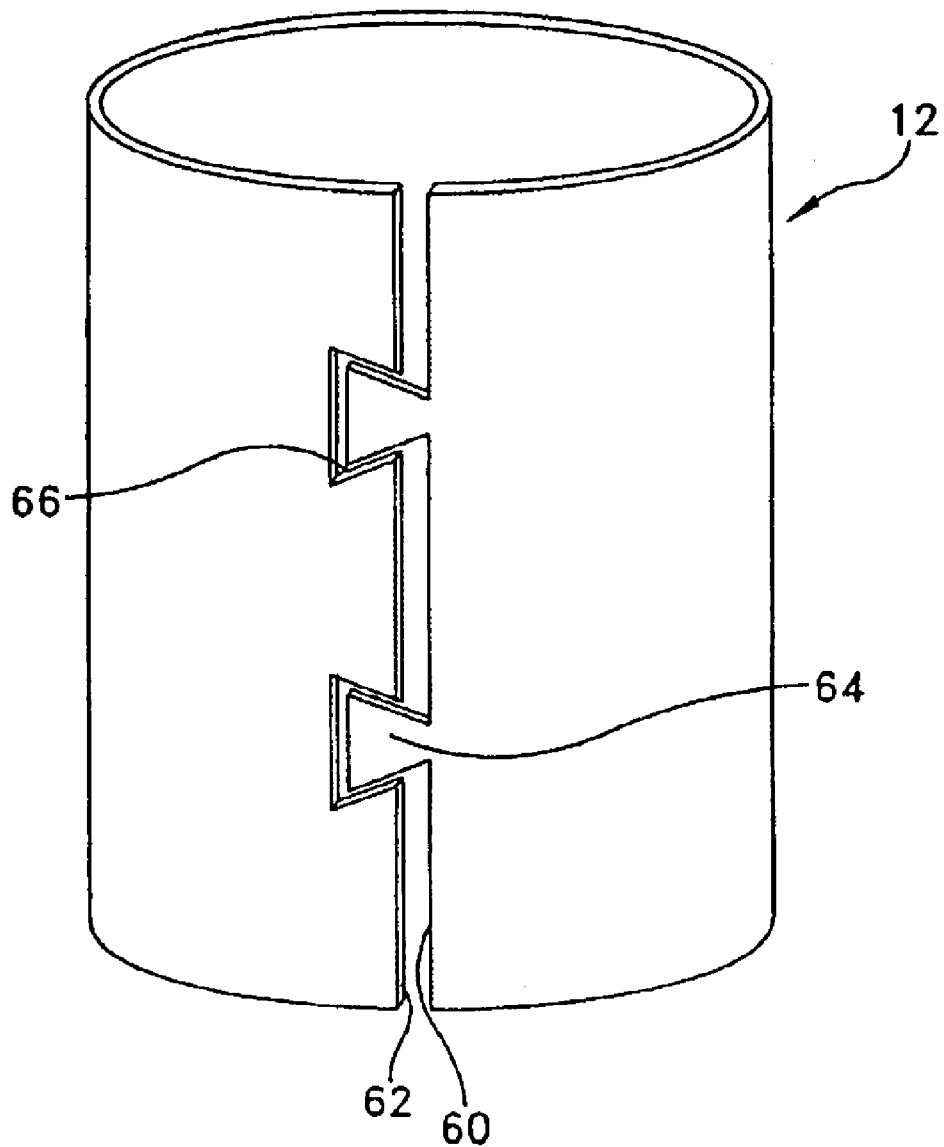
FIG. 13 is a perspective view of an alternative embodiment of the anchor tubular body portion.

The tubular body 12 shown in FIGS. 2–9 may be substantially rigid or may be slightly expandable to enable the tubular body to more snugly engage the bone when expansion device 24 is set within the tubular body. In the latter case, the expansion capability may be provided for by having the tubular body 12 formed out of a plastic material, or by providing, in an otherwise substantially rigid body, a mechanical means for permitting expansion. In this latter regard, there is shown in FIG. 13 a tubular body 12 having opposed lengthwise free edges 60, 62 having tongues 64 and grooves 66 formed thereon, respectively. Limited expansion of the tubular body 12 is permitted within the confines of the tongue-and-groove arrangement.

It should be appreciate that, by providing (1) tubular body 12, and (2) an external flange 20 or external screw threads 44 for stabilizing tubular body 12 relative to the adjacent bone, and (3) deformable walls 22, 22a, or ligament carrier 32, and expansion device 24 for making the graft ligament fast to tubular body 12, the graft ligament L can be securely attached to a host bone. This is true regardless of whether such attachment is to relatively hard outer cortical bone, or to relatively soft inner cancellous bone, or even where the host bone has relatively poor bone quality.

It should also be appreciated that, while in the foregoing description the graft ligament anchor of the present invention has been discussed in the context of attaching one end of a graft ACL to the tibia, the graft ligament anchor could also be used to attach one end of the graft ACL to the femur, or to attach a graft ligament to another bone in the body.

It should also be appreciated that, with respect to the graft ligament anchor shown in FIGS. 9–12, ligament carrier 32 might be omitted altogether, and expansion device 24 might be used to attach the graft ligament L directly to the side wall of tubular body 12. Of course, in such a situation, since expansion device 24 will be directly engaging graft ligament L, it is important that expansion device 24 be constructed so that it will not cut or otherwise damage graft ligament L. In such a situation, expansion device 24 might comprise a so-called "non-cutting interference screw" of sort manufactured by Arthrex.

Furthermore, it should also be appreciated that, with respect to the graft ligament anchor embodiments shown in FIGS. 9–12, tubular body 12 might be omitted altogether, and ligament carrier 32 might be used to attach the graft ligament L directly to the side wall of the bone tunnel. Of course, in such a situation, the attachment of the graft ligament L to the host bone might be somewhat less secure than where tubular body 12 is used, particularly where the host bone is relatively soft cancellous bone or where the host bone is of relatively poor bone quality. Furthermore, in such a situation, it might be desirable to increase the size of the ligament carrier's detents 48 so that they can act as stops to prevent the ligament carrier from being drawn into the bone tunnel due to ligament tension.

Thus there is provided an improved graft ligament anchor which is simple in construction, inexpensive to manufacture, easy to handle and install, and reliable and safe in operation.

In addition, the graft ligament anchor can easily and reliably anchor a graft ligament in a bone of relatively poor quality.

There is further provided an improved method for attaching a graft ligament to a bone.

It is to be understood that the present invention is by no means limited to the particular constructions and methods herein disclosed and/or shown in the drawings, but also comprises any modifications or equivalents within the scope of the claims. For example, in illustrative embodiments described hereinabove, ligament carrier 32 is illustrated with external ridges 35 (FIG. 9), tubular body 12 is illustrated with interior ridges 39 (FIG. 5), an expansion device 24 is provided with ridges 58 (FIG. 12). It will be apparent to those skilled in the art that such ridges effect a gripping facility by virtue of providing a textured surface. Appropriate and useful surfaces may be rendered "textured" by means other than, or in addition to, ridges, such as by lands, grooves, steps, teeth, apertures, roughened portions, and the like. Among other things, it has been found that graft ligament fixation can be improved where such textured surfaces cause the graft ligament to assume a somewhat convoluted or tortuous path on a localized basis, e.g., as the graft ligament extends over a series of adjacent ridges.

What is claimed is:

1. A graft ligament anchor comprising:
    a tubular body having a bore therethrough and proximal and distal ends;
    an annular flange attached to said tubular body at the proximal end thereof and extending radially outwardly beyond said body;
    a deformable wall mounted on an inside surface of the tubular body bore and in conjunction with the tubular body inside surface defining a chamber extending lengthwise of said tubular body for receiving a graft ligament therein; and
    an expansion device for insertion into said tubular body, axially of said tubular body, for impinging upon said deformable wall so as to press said deformable wall, and hence the graft ligament received in the chamber, toward the tubular body inside surface, whereby to fix the graft ligament in said tubular body.

2. A graft ligament anchor according to claim 1 wherein said graft ligament anchor comprises a further deformable wall, each of said deformable walls defining in part of a chamber, each of the chambers being adapted to retain a graft ligament therein.

3. A graft ligament anchor according to claim 2 wherein said expansion device comprises a wedge-shaped device for insertion between opposed ones of said deformable walls so as to press said opposed deformable walls outwardly from each other and toward the inside surface of the bore.

4. A graft ligament anchor according to claim 3 wherein said wedge-shaped device comprises a screw.

5. A graft ligament anchor according to claim 1 wherein said tubular body is provided with an opening extending through a side of said body and said chamber.

6. A graft ligament anchor according to claim 5 wherein said opening comprises an elongated slot.

7. A graft ligament anchor according to claim 1 wherein a pair of arms extend axially and proximally from the proximal end of said body, and said annular flange is fixed to proximal ends of said arms.

8. A graft ligament anchor according to claim 7 wherein said body is provided with an opening through a side wall thereof and extending into the chamber.

9. A graft ligament anchor according to claim 1 wherein said expansion device is adapted to press the graft ligament in the chamber against the inside surface of the tubular body bore.

10. A graft ligament anchor according to claim 1 wherein said tubular body is provided with interior ridges disposed on the inside surface of the bore.

11. A graft ligament anchor according to claim 1 wherein said tubular body is expandable width-wise.

12. A graft ligament anchor according to claim 3 wherein said wedge-shaped device is provided with a textured surface.

13. A graft ligament anchor according to claim 3 wherein said wedge-shaped device comprises a mandrel.

14. A method for securing a graft ligament in a bone tunnel having an end opening on a bone surface, a free end of the graft ligament extending out of the bone tunnel end opening, the method comprising the steps of:
  providing a graft ligament anchor comprising:
    a tubular body having a bore therethrough and proximal and distal ends, said tubular body being adapted for placement in a bone tunnel proximate an opening thereof on a bone surface;
    stop apparatus connected to said tubular body for preventing movement of said tubular body further into the bone tunnel after placement of said tubular body in the opening and the bone tunnel; and
    an expansion device for insertion into said tubular body axially of said tubular body, for impinging upon the graft ligament so as to press the graft ligament toward the tubular body, whereby to fix the graft ligament in the tubular body;
  extending the graft ligament free end through said tubular body;
  placing said tubular body in the end opening and in the bone tunnel such that said stop apparatus engages the bone;
  pulling the graft ligament taut; and
  inserting said expansion device into said tubular body and advancing said expansion device therein to press the graft ligament toward the wall of the bore, whereby to fix the graft ligament in the bone tunnel.

15. A graft ligament anchor comprising:
  a tubular body having a bore therethrough ad proximal and distal ends;
  an annular flange attached to said tubular body at the proximal end thereof and extending radially outwardly beyond said body;
  a plurality of deformable walls, each defining at least in part a chamber, each of the chambers being adapted to retain a graft ligament therein;
  an expansion device for insertion into said tubular body, axially of said body, for impinging upon said deformable walls so as to press said deformable walls, and hence the graft ligaments received in the chambers, toward a wall of the bore, whereby to fix the graft ligament in the tubular body;
  wherein said expansion device comprises a wedge-shaped screw for insertion between opposed ones of said deformable walls so as to press said opposed deformable walls outwardly from each other and toward the wall of the bore.

16. A graft ligament anchor according to claim 15 wherein said tubular body is provided with openings, each extending through a side of said body and a chamber.

17. A graft ligament anchor according to claim 16 wherein the openings each comprise an elongated slot.

18. A graft ligament anchor comprising:
  a tubular body having a bore therethrough and proximal and distal ends;
  an annular flange attached to said tubular body at the proximal end thereof and extending radially outwardly beyond said body;
  a deformable wall disposed in the tubular body bore and defining, at least in part, a chamber for receiving a graft ligament therein; and
  an expansion device for insertion into said tubular body, axially of said body, for impinging upon said deformable wall so as to press said deformable wall, and hence the graft ligament received in the chamber, toward a wall of the bore, whereby to fix the graft ligament in the tubular body;
  wherein a pair of arms extend axially and proximally from the proximal end of said body, and said annular flange is fixed to proximal ends of said arms; and
  wherein said body is provided with an opening through a side wall thereof and extending into the chamber.

19. A graft ligament anchor comprising:
  a tubular body having a bore therethrough and proximal and distal ends;
  an annular flange attached to said tubular body at the proximal end thereof and extending radially outwardly beyond said body;
  a deformable wall disposed in the tubular body bore and defining, at least in part, a chamber for receiving the graft ligament therein; and
  an expansion device for insertion into said tubular body, axially of said body, for impinging upon said deformable wall so as to press said deformable wall, and hence the graft ligament received in the chamber, toward a wall of the bore, whereby to fix the graft ligament in said tubular body;
  wherein said tubular body is provided with interior ridges disposed on the wall of the bore.

20. A graft ligament anchor comprising:
  a tubular body having a bore therethrough and proximal and distal ends;
  an annular flange attached to said tubular body at said proximal end thereof and extending radially outwardly beyond said body;
  deformable walls, each defining at least in part a chamber, each of the chambers being adapted to retain a graft ligament therein;

an expansion device for insertion into said tubular body, axially of said body, for impinging upon said deformable walls so as to press said deformable walls, and hence the graft ligaments received in the chambers, toward a wall of the bore, whereby to fix the graft ligaments in the tubular body;

wherein said expansion device comprises a wedge-shaped device for insertion between opposed ones of said deformable walls so as to press said opposed deformable walls outwardly from each other and toward the wall of the bore; and wherein said wedge-shaped device is provided with a textured surface.

21. A graft ligament anchor comprising:

a tubular body having a bore therethrough and proximal and distal ends;

an annular flange attached to said tubular body at said proximal end thereof and extending radially outwardly beyond said body;

deformable walls, each defining at least in part a chamber, each of the chambers being adapted to retain a graft ligament therein;

an expansion device for insertion into said tubular body, axially of said body, for impinging upon said deformable walls so as to press said deformable walls, and hence the graft ligaments received in said chambers, toward a wall of said bore, whereby to fix the graft ligament in the tubular body;

wherein said expansion device comprises a wedge-shaped device for insertion between opposed ones of said deformable walls so as to press said opposed deformable walls outwardly from each other and toward said wall of said bore; and wherein said wedge-shaped device comprises a mandrel.

* * * * *